United States Patent [19]

Fabry et al.

[11] Patent Number: 5,319,117
[45] Date of Patent: Jun. 7, 1994

[54] PROCESS FOR THE SULFONATION OF UNSATURATED FATTY ACID GLYCEROL ESTERS

[75] Inventors: Bernd Fabry, Korschenbroich; Michael Schaefer, Erkrath; Hermann Anzinger, Duesseldorf, all of Fed. Rep. of Germany

[73] Assignee: Henkel Kommanditgesellschaftr auf Aktien, Duesseldorf, Fed. Rep. of Germany

[21] Appl. No.: 849,400

[22] PCT Filed: Oct. 19, 1990

[86] PCT No.: PCT/EP90/01778
§ 371 Date: Apr. 24, 1992
§ 102(e) Date: Apr. 24, 1992

[87] PCT Pub. No.: WO91/06532
PCT Pub. Date: May 16, 1991

[30] Foreign Application Priority Data

Oct. 28, 1989 [DE] Fed. Rep. of Germany ....... 3936001

[51] Int. Cl.$^5$ ................................................ C11D 1/28
[52] U.S. Cl. ......................................... 554/98; 554/97
[58] Field of Search ..................................... 554/97, 98

[56] References Cited

U.S. PATENT DOCUMENTS 3,969,375  7/1976  Okumura et al. ................. 554/97
4,579,687  4/1986  Sekiguchi et al. ................. 554/97

FOREIGN PATENT DOCUMENTS 2437443  2/1975  Fed. Rep. of Germany .
3437443  4/1986  Fed. Rep. of Germany .
475391  11/1975  U.S.S.R. .
793427  4/1958  United Kingdom .

OTHER PUBLICATIONS

Chemical Abstracts, vol. 100, No. 12, 1984, p. 105, abstract No. 87651t, & Pl, A 120411, 1983.
J. Falbe (ed.), Surfactants in Consumer Products, Springer-Verlag, 1987, pp. 61–63.
H. Stache, H. Grossman, Waschmittel, Springer-Verlag, 1985, Article unavailable.
Soap. Cosm. Chem. Spec., 1975, p. 39, Article unavailable.

*Primary Examiner*—José G. Dees
*Assistant Examiner*—Deborah D. Carr
*Attorney, Agent, or Firm*—Ernest G. Szoke; Wayne C. Jaeschke; Henry E. Millson, Jr.

[57] ABSTRACT

Process for the production of aqueous solutions of alkali metal, alkaline earth metal, ammonium and/or amine salts of sulfonated fatty acid glycerides by sulfonation of unsaturated fatty acid glycerol esters with gaseous sulfur trioxide, neutralization with aqueous bases and subsequent heating with phase separation, and to the aqueous solutions produced thereby.

20 Claims, No Drawings

PROCESS FOR THE SULFONATION OF UNSATURATED FATTY ACID GLYCEROL ESTERS

BACKGROUND OF THE INVENTION

1. Field of the Invention

This invention relates to a process for the production of aqueous solutions of alkali metal, alkaline earth metal, ammonium and/or amine salts of sulfonated fatty acid glycerides by sulfonation of unsaturated fatty acid glycerol esters with gaseous sulfur trioxide, neutralization with bases and subsequent heating with phase separation and to their use as surfactants.

2. Description of Related Art

Sulfonation products based on unsaturated fatty acid glycerol esters have long been known. As long ago as 1834, Runge obtained sulfonated oils by the action of sulfuric acid on olive oil or castor oil. These oils are still in use today as auxiliaries, so-called "Turkey red oils", in the dyeing of textiles (H. Stache, H. Grossmann, "Waschmittel", Springer-Verlag, Berlin-Heidelberg, 1985). Other sulfonated oils are used in the wet finishing of textiles, in hand-washing pastes, as thickeners in paints, as hydrotropes for liquid detergents, corrosion inhibitors or emulsifiers for mineral oils (Soap. Cosm. Chem. Spec. (1975) 39).

The two patent applications PL 120 511 and SU 475 391 describe processes for reacting unsaturated triglycerides, for example from the oleic-acid-rich fraction of tall oil, with sulfuric acid. The addition of $H_2SO_4$ onto the double bond of unsaturated fatty acid glycerol esters leads to the formation of sulfates which are characterized by —C—O—S— bonds and hence are labile to the aggressive effect of acids. Accordingly, the use of products such as these is confined to the neutral to mildly alkaline range.

Alternatively, the sulfonation reaction also be carried out with oleum, i.e. with sulfur trioxide which is dissolved in sulfuric acid in a concentration of up to 65% by weight. Although, in addition to the formation of sulfates, this process leads mainly to the formation of sulfonates having an acid-stable —C—S— bond, it is attended by the serious disadvantage that the sulfuric acid used as solvent has to be neutralized together with the sulfonic acids obtained so that the products are burdened by an undesirably high electrolyte content which is problematical in many applications.

German patent application DE 12 46 717 describes the sulfonation of unsaturated fatty acid glycerol esters with gaseous sulfur trioxide in admixture with an inert gas. However, since undesirably strong discoloration of the products is observed in addition to sulfonation with increasing reaction temperature and quantity of $SO_3$ and can lead to carbonization in cases where the sulfonating agent is used in relatively large quantities, the process is confined in its application to temperatures in the range from 0 to 20° C. and to ratios of fatty acid ester to sulfur trioxide of 1:0.5 to 1:1.7. Accordingly, it is only possible in this way to obtain sulfonation products of unsaturated fatty acid glycerol esters which have a low content of organically bound sulfur.

Finally, German patent application DE 34 37 443 A1 describes a process for reacting both unsaturated fatty acid glycerol esters and saturated fatty acid esters with gaseous sulfur trioxide. However, the disadvantage of this process is that the production of homogeneous mixtures of both components involves considerable outlay on equipment, in addition to which the sulfonation products have a high percentage content of α-fatty acid methyl ester sulfonates.

DESCRIPTION OF THE INVENTION

The problem addressed by the present invention was to provide a process for the sulfonation of unsaturated fatty acid glycerol esters which, after neutralization, would lead to low-viscosity, light-colored products having a high percentage content of organically bound sulfur and a high sulfonate content.

The present invention relates to a process for the production of aqueous solutions of alkali metal, alkaline earth metal, ammonium and/or amine salts of sulfonated fatty acid glycerides by sulfonation of unsaturated fatty acid glycerol esters with gaseous sulfur trioxide, subsequent neutralization with bases and subsequent heating, in which unsulfonated components can be separated from the aqueous surfactant solution by phase separation.

In the context of the invention, fatty acid glycerol esters are understood to be the monoesters, diesters and triesters and mixtures thereof which are obtained where production is carried out by esterification of mol glycerol with 1 to 3 mol unsaturated fatty acid or in the transesterification of unsaturated triglycerides with 0.3 to 2 mol glycerol. More particularly, the fatty acid glycerol esters used are unsaturated fatty acid glycerol esters formed from fatty acids containing 16 to 24 carbon atoms and 1 to 5 double bonds, for example from palmitoleic acid, elaidic acid, petroselic acid, chaulmoogric acid, erucic acid, linolenic acid, arachidonic acid or clupanodonic acid, but especially from oleic acid and linoleic acid which preferably make up more than 50% by weight of the fatty acid component.

The fatty acid glycerol esters may be of synthetic or natural origin. It is preferred to use esters based on coriander oil, chaulmoogra oil, sunflower oil, cottonseed oil, olive oil, peanut oil, linseed oil, lard oil, meadowfoam oil, lard or fish oil, but especially new rapeseed oil rich in oleic acid. Specifically, it is also possible to use native fatty acid glycerol esters of which the fatty acid component does not consist entirely, but only predominantly, i.e. to a level of more than 50% by weight, of the unsaturated fatty acids mentioned and also technical mixtures of various unsaturated or substantially unsaturated fatty acid glycerol esters with one another providing the content of unsaturated fatty acids in the mixture is again more than 50% by weight. New rapeseed oil rich in oleic acid is preferably used.

The sulfonation of the unsaturated fatty acid glycerol esters with gaseous sulfur trioxide may be carried out by the method known for fatty acid lower alkyl esters (J. Falbe (ed.), "Surfactants in Consumer Products", Springer Verlag, Berlin-Heidelberg, 1987, page 61), reactors operating on the falling-film principle being preferred. In this method, the sulfur trioxide is diluted with a inert gas, preferably air or nitrogen, and is used in the form of a gas mixture containing the sulfonating agent in a concentration of 1 to 8% by volume and, more particularly, 2 to 5% by volume.

The gaseous sulfur trioxide is used in a ratio of 0.5 to 5 mol and preferably 1.0 to 3.0 mol sulfur trioxide per mol fatty acid glycerol ester. The sulfonation reaction is carried out at temperatures of 40 to 98° C. and, more particularly, at temperatures of 50 to 90° C.

The acidic sulfonation products obtained in the sulfonation reaction are stirred into aqueous bases, neutralized and adjusted to a pH value of 6.5 to 8.5. Bases suitable for neutralization are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, di- and tri-$C_{2-4}$-alkanolamines, for example mono-, di- and triethanolamine, and also primary, secondary or tertiary $C_{1-4}$ alkyl amines. The neutralization bases are preferably used in the form of 5 to 55% by weight aqueous solutions, 5 to 25% by weight aqueous sodium hydroxide solutions being preferred.

The aqueous solutions containing the neutralized sulfonation products are then heated on a steam bath for 10 to 240 minutes and preferably for 30 to 120 minutes at a temperature of 80 to 95° C. The reaction mixture separates into an aqueous phase containing the surface-active compound and an organic phase containing unsulfonated starting product which can be separated from one another very easily, for example by decantation or separation. After drying, the organic phase, which contains only traces of water, may be reused for sulfonation. In this way, products having a high content of organically bound sulfur are obtained, even where small quantities of sulfur trioxide are used. An additional advantage is that the products obtained in this way are distinguished by particularly light colors.

The sulfonation product is a complex mixture essentially containing mono-, di- and triglyceride sulfonates containing an internal sulfonic acid group. Sulfonated fatty acids, glyceride sulfates, glycerol sulfates, glycerol and soaps are formed as secondary products.

After neutralization, the sulfonation products may be bleached in known manner by addition of hydrogen peroxide or sodium hypochlorite solution. 0.2 to 2% by weight hydrogen peroxide, expressed as 100% substance or corresponding quantities of sodium hypochlorite are used, based on the solids content in the solution of the sulfonation products. The pH value of the solutions may be kept constant using suitable buffers, for example sodium phosphate or citric acid. In addition, it is advisable to add preservatives, for example formaldehyde solution, p-hydroxybenzoate, sorbic acid or other known perservatives, for stabilization against bacterial infestation.

The present invention also relates to the use of the products obtainable by reaction of unsaturated fatty acid glycerol esters with gaseous sulfur trioxide after neutralization as surfactants.

The following Examples are intended to illustrate the invention.

EXAMPLES

TABLE 1

| | Composition of the triglycerides (educts) used FIGS. in % by weight | | | | | | | | | |
|---|---|---|---|---|---|---|---|---|---|---|
| Fatty acid | Olv % | NSf % | Cor % | Pnt % | Soy % | NRp % | Lin % | Mdw % | Lrd % | Fsh % |
| Myristic acid | 10 | — | — | — | — | 1 | — | — | 1 | 7 |
| Palmitic acid | 3 | 4 | 4 | 10 | 8 | — | 5 | — | 29 | 14 |
| Palmitoleic acid | — | — | — | — | 1 | 4 | 4 | — | 3 | 11 |
| Stearic acid | — | 4 | — | 3 | 4 | 1 | — | — | 13 | 1 |
| Oleic acid | 80 | 85 | 3 | 50 | 28 | 59 | 22 | 2 | 47 | 15 |
| Petroselic acid | — | — | 80 | — | — | — | — | — | — | — |
| Linoleic acid | 7 | 7 | 13 | 30 | 52 | 20 | 17 | 1 | 6 | 3 |
| Linolenic acid | — | — | — | — | 6 | 9 | 52 | — | 1 | 1 |
| Arachic acid | — | — | — | 3 | 1 | 1 | — | 1 | — | — |
| Gadoleic acid | — | — | — | — | — | 2 | — | 63 | — | — |
| Behenic acid | — | — | — | 2 | — | 1 | — | — | — | — |
| Erucic acid | — | — | — | — | — | 1 | — | 15 | — | — |
| Docosadienoic acid | — | — | — | — | — | — | — | 18 | — | — |
| Arachidonic acid | — | — | — | — | — | — | — | — | — | 25 |
| Clupanodonic acid | — | — | — | — | — | — | — | — | — | 23 |
| Lignoceric acid | — | — | — | 2 | — | — | — | — | — | — |
| Iodine value* | 88 | 92 | 88 | 100 | 141 | 120 | 205 | 133 | 57 | 142 |
| Saponification value | 196 | 195 | 196 | 195 | 195 | 190 | 196 | 199 | 202 | 194 |

Legend:
Olv = Olive oil
NSf = New sunflower oil (<80% by weight oleic acid)
Cor = Coriander oil
Pnt = Peanut oil
Soy = Soybean oil
NRp = New rapeseed oil (>55% by weight oleic acid)
Lin = Linseed oil
Mdw = Meadowfoam oil
Lrd = Lard oil
Fsh = Fish oil

*Composition as determined by GC analysis, evaluation as area-%. The iodine value was determined by the Kaufmann method.

EXAMPLES 1.1–1.21

General Procedure Method A: Batch Sulfonation of Fatty Acid Glycerol Esters

Quantities of 1 mol of the unsaturated fatty acid glycerol ester were introduced into a 1-liter sulfonation reactor with jacket cooling and reacted with 0.5 to 5.0 mol gaseous sulfur trioxide at 40 to 98° C. The sulfur trioxide had been driven out by heating from a corresponding quantity of 65% oleum, diluted to a concentration of 2 to 5% by volume and introduced into the starting product over a period of 15 to 120 minutes. After sulfonation, the acidic reaction mixture was stirred in portions into aqueous 10% by weight base, neutralized and heated on a steam bath for 120 minutes at 95° C, the solution separating into an aqueous surfactant phase and an organic phase containing unreacted starting material. After phase separation in a separation funnel, the organic fraction was dried in vacuo for 2 h at 80° C. and returned to the sulfonation reaction. The aqueous surfactant solution was adjusted to pH 7.8 and had a solids content of 30%. Table 2 provides an overview of the fatty acid glycerol esters used, the reaction conditions and the characteristic data of the products.

EXAMPLES 2.1–2.14

General Procedure Method B: Continuous Sulfonation of Fatty Acid Glycerol Esters 5.0 mol of an unsaturated fatty acid glycerol ester were reacted with 5 to 15 mol gaseous sulfur trioxide at 40 to 98° C. in a continuous falling-film reactor (length 120 cm, cross-section 1 cm, educt throughput 600 g/h) with jacket cooling and lateral introduction of $SO_3$. The acidic reaction mixture was continuously introduced into 10% by weight base and neutralized. The product was heated on a steam bath for 120 minutes at 95° C., the solution separating into an aqueous surfactant phase and an organic phase containing unreacted starting material. After phase separation in a separation funnel, the organic fraction was dried in vacuo for 2 h at 80° C. and returned to the sulfonation reaction. The aqueous surfactant solution was adjusted to pH 7.8 and had a solids content of 30%. Table 3 provides an overview of the fatty acid glycerol esters used, the reaction conditions and the characteristic data of the products.

The anionic surfactant content (WAS) and the unsulfonated components (US) were determined in accordance with the DGF-Einheitsmethoden (DGF Standard Methods), Stuttgart 1950–1984, H-III-10 and G-II-6b. The Klett color value was determined after bleaching for 30 minutes with 1% by weight of a 35% by weight aqueous hydrogen peroxide solution. The measurement was carried out at a concentration of 5% by weight anionic surfactant, pH=7 and using a 1 cm round cuvette and a blue filter (400 to 465 nm).

TABLE 2

| | | | | | | | | | |
|---|---|---|---|---|---|---|---|---|---|
| Characteristic data of the Examples of method A | | | | | | | | | |
| Ex. | Educt | $SO_3$ mol | Vd. % | T °C. | Rct mins. | Base | WAS Meq/g | US % | $SO_4^{2-}$ % | Color Klett |
| 1.1 | NRp | 2.0 | 2 | 80 | 48 | NaOH | 0.444 | 1.8 | 2.9 | 146 |
| 1.2 | NRp | 2.0 | 5 | 80 | 68 | NaOH | 0.444 | 2.8 | 2.7 | 158 |
| 1.3 | Olv | 2.0 | 2 | 80 | 48 | NaOH | 0.337 | 2.8 | 3.9 | 125 |
| 1.4 | Olv | 2.0 | 5 | 80 | 68 | NaOH | 0.334 | 2.8 | 3.7 | 132 |
| 1.5 | NSf | 2.0 | 2 | 80 | 48 | NaOH | 0.337 | 2.8 | 3.8 | 115 |
| 1.6 | NSf | 2.0 | 5 | 80 | 68 | NaOH | 0.338 | 2.8 | 3.2 | 119 |
| 1.7 | NRp | 0.5 | 5 | 50 | 18 | NaOH | 0.225 | 4.7 | 0.5 | 98 |
| 1.8 | NRp | 1.0 | 5 | 50 | 32 | NaOH | 0.225 | 4.1 | 1.1 | 122 |
| 1.9 | NRp | 1.5 | 5 | 50 | 51 | NaOH | 0.339 | 3.3 | 1.8 | 131 |
| 1.10 | NRp | 2.0 | 5 | 50 | 77 | NaOH | 0.339 | 3.6 | 2.4 | 149 |
| 1.11 | NRp | 0.5 | 5 | 90 | 15 | NaOH | 0.225 | 4.5 | 3.4 | 105 |
| 1.12 | NRp | 1.0 | 5 | 90 | 29 | NaOH | 0.224 | 4.1 | 0.7 | 127 |
| 1.13 | NRp | 1.5 | 5 | 90 | 45 | NaOH | 0.203 | 3.6 | 2.4 | 145 |
| 1.14 | NRp | 2.0 | 5 | 90 | 65 | NaOH | 0.334 | 3.1 | 2.7 | 160 |
| 1.15 | NRp | 2.5 | 5 | 90 | 73 | NaOH | 0.336 | 2.2 | 3.4 | 201 |
| 1.16 | NRp | 3.0 | 5 | 90 | 91 | NaOH | 0.446 | 1.9 | 3.4 | 261 |
| 1.17 | NRp | 4.0 | 5 | 90 | 108 | NaOH | 0.339 | 1.5 | 4.8 | 309 |
| 1.18 | NRp | 5.0 | 5 | 90 | 120 | NaOH | 0.446 | 0.7 | 5.1 | 396 |
| 1.19 | NRp | 2.0 | 5 | 90 | 65 | KOH | 0.335 | 2.9 | 2.5 | 155 |
| 1.20 | NRp | 2.0 | 5 | 90 | 65 | $NH_3$ | 0.299 | 2.8 | 2.6 | 167 |
| 1.21 | NRp | 2.0 | 5 | 90 | 65 | DEA | 0.341 | 2.9 | 2.3 | 169 |

Legend:
$SO_3$ = quantity used mol $SO_3$/mol educt
Vd. = $SO_3$ concentration in the inert gas stream (% by vol.)
Rct = reaction time
WAS = anionic surfactant content
US = unsulfonated (% by weight)
$SO_4^{2-}$ = sulfate, expressed as sodium sulfate (% by weight)
DEA = diethanolamine
The products of Examples 1.1 to 1.21 had a water content of 70% by weight.

TABLE 3

| | | | | | | | | | |
|---|---|---|---|---|---|---|---|---|---|
| Characteristic data of the Examples of method B | | | | | | | | | |
| Ex. | Educt | $SO_3$ mol | Vd. % | T °C. | Rct mins. | Base | WAS Meq/g | US % | $SO_4^{2-}$ % | Color Klett |
| 2.1 | NRp | 1.0 | 5 | 90 | — | NaOH | 0.223 | 4.6 | 3.4 | 112 |
| 2.2 | NRp | 2.0 | 5 | 90 | — | NaOH | 0.333 | 2.9 | 3.0 | 154 |
| 2.3 | NRp | 3.0 | 5 | 90 | — | NaOH | 0.445 | 1.8 | 3.3 | 244 |
| 2.4 | Olv | 2.0 | 5 | 90 | — | NaOH | 0.335 | 2.7 | 3.6 | 121 |
| 2.5 | NSf | 2.0 | 5 | 90 | — | NaOH | 0.331 | 2.8 | 3.0 | 110 |
| 2.6 | Cor | 2.0 | 5 | 90 | — | NaOH | 0.335 | 2.8 | 3.0 | 112 |
| 2.7 | Pnt | 2.0 | 5 | 90 | — | NaOH | 0.337 | 2.9 | 3.4 | 136 |
| 2.8 | Soy | 2.0 | 5 | 90 | — | NaOH | 0.336 | 2.9 | 3.6 | 168 |
| 2.9 | Lin | 2.0 | 5 | 90 | — | NaOH | 0.335 | 3.1 | 4.0 | 208 |
| 2.10 | Lrd | 2.0 | 5 | 90 | — | NaOH | 0.337 | 2.8 | 3.0 | 159 |
| 2.11 | Mdw | 2.0 | 5 | 90 | — | NaOH | 0.335 | 2.8 | 3.2 | 185 |
| 2.12 | Fsh | 1.0 | 5 | 90 | — | NaOH | 0.114 | 5.0 | 3.1 | 396 |
| 2.13 | Fsh[1] | 2.0 | 5 | 90 | — | NaOH | 0.329 | 4.1 | 2.9 | >800 |
| 2.14 | Fsh[2] | 2.0 | 5 | 90 | — | NaOH | 0.330 | 2.8 | 6.0 | >800 |

[1]Mixture of 90% by weight fish oil + 10% by weight new rapeseed oil
[2]Mixture of 50% by weight fish oil + 50% by weight new rapeseed oil
The products of Example 2.1 to 2.14 had a water content of 70% by weight.

We claim:

1. A process for the preparation of an aqueous solution of at least one alkali metal, alkaline earth metal, ammonium, or amine salt of a sulfonated fatty acid glyceride containing only internal sulfonate groups, comprising the steps of:
   A) reacting a composition consisting essentially of an unsaturated fatty acid glycerol ester or a mixture of such esters with gaseous sulfur trioxide,
   B) neutralizing the resulting reaction mixture with an aqueous base,
   C) heating the neutralized mixture from step B at a temperature and for a time sufficient to separate the neutralized mixture into an aqueous phase and an organic phase, and
   D) separating the aqueous phase from the organic phase.

2. The process of claim 1 wherein the step A the unsaturated fatty acid glycerol ester is at least one ester in which the percentage content of unsaturated fatty acid is greater than 50% by weight.

3. The process of claim 2 wherein the ester is new rapeseed oil rich in oleic acid.

4. The process of claim 1 wherein the unsaturated fatty acid glycerol ester in step A is at least one monoglyceride, diglyceride, or triglyceride containing a $C_{16-24}$ fatty acid having 1 to 5 double bonds.

5. The process of claim 4 where in the unsaturated fatty acid glycerol ester more than 50% by weight of the fatty acid component thereof consists of oleic acid, linoleic acid or both.

6. The process of claim 1 wherein step A is carried out in a falling film reactor in which the gaseous sulfur trioxide is diluted with an inert gas to a concentration of sulfur trioxide of from about 1 to about 8% by volume.

7. The process of claim 6 wherein said concentration is from about 2 to about 5% by volume.

8. The process of claim 1 wherein step A the sulfur trioxide is used in a ratio of about 0.5 to about 5.0 mols per mol of unsaturated fatty acid glycerol ester and the sulfonation temperature is in the range of from about 40° to about 98° C.

9. The process of claim 8 wherein the sulfur trioxide is used in a ratio of about 1.0 to about 3.0 mols per mol of unsaturated fatty acid glycerol ester and the sulfonation temperature is in the range of from about 50° to about 90° C.

10. The process of claim 1 wherein step B is carried out with an aqueous base containing from about 5 to about 55% by weight of an alkali metal hydroxide, an alkaline earth metal oxide or hydroxide, ammonia, a mono-, di-, or tri-$C_{2-4}$-alkanolamine, or a primary, secondary or tertiary $C_{1-4}$ alkyl amine.

11. The process of claim 1 wherein in step C the neutralized mixture is heated for from about 10 to about 240 minutes at a temperature of from about 80° to about 98° C.

12. The process of claim 11 wherein the neutralized mixture is heated for from about 30 to about 120 minutes at a temperature of from about 90° to about 95° C.

13. The process of claim 1 wherein in step D the organic phase is dried and returned to step A.

14. A process for the preparation of an aqueous solution of at least one alkali metal, alkaline earth metal, ammonium, or amine salt of a sulfonated fatty acid glyceride containing only internal sulfonate groups, comprising the steps of:
   A) reacting a composition consisting essentially of an unsaturated fatty acid glycerol ester or a mixture of such esters in which the percentage content of unsaturated fatty acid in the glycerol esters is greater than 50% by weight with gaseous sulfur trioxide at a temperature in the range of from about 40° to about 98° C., wherein the sulfur trioxide is present in a ratio of about 0.5 to about 5.0 mols per mol of unsaturated fatty acid glycerol ester,
   B) neutralizing the reaction mixture from step A with an aqueous base containing from about 5 to about 55% by weight of an alkali metal hydroxide, an alkaline earth metal oxide or hydroxide, ammonia, a mono-, di-, or tri-$C_{2-4}$-alkanolamine, or a primary, secondary or tertiary $C_{1-4}$ alkyl amine,
   C) heating the neutralized mixture from step B for from about 10 to about 240 minutes at a temperature of from about 80° to about 98° C. to separate the neutralized mixture into an aqueous phase and an organic phase, and
   D) separating the aqueous phase from the organic phase.

15. The process of claim 14 wherein the unsaturated fatty acid glycerol ester in step A is at least one monoglyceride, diglyceride, or triglyceride containing a $C_{16-24}$ fatty acid having 1 to 5 double bonds.

16. The process of claim 4 wherein in the unsaturated fatty acid glycerol ester more than 50% by weight of the fatty acid component thereof consists of oleic acid, linoleic acid, or both.

17. The process of claim 14 wherein step A is carried out in a falling film reactor in which the gaseous sulfur trioxide is diluted with an inert gas to a concentration of sulfur trioxide of from about 1 to about 8% by volume.

18. The process of claim 14 wherein in step A sulfur trioxide is present in a ratio of about 1.0 to about 3.0 mols per mol of unsaturated fatty acid glycerol ester and the sulfonation temperature is in the range of from about 50° to about 90° C, and in step C the neutralized mixture is heated for from about 30 to about 120 minutes at a temperature of from about 90° to about 95° C.

19. The aqueous solution obtained by the process of claim 1.

20. The aqueous solution obtained by the process of claim 14.

* * * * *